United States Patent [19]

Lesher, deceased et al.

[11] Patent Number: 5,010,086
[45] Date of Patent: Apr. 23, 1991

[54] IMIDAZOPYRIDINES, COMPOSITIONS AND USE

[75] Inventors: George Y. Lesher, deceased, late of Schodack, by Louise E. Lesher, executrix; Edward R. Bacon, East Greenbush; Baldev Singh, East Greenbush; Gee-Hong Kuo, East Greenbush, all of N.Y.

[73] Assignee: Sterling Drug Inc., New York, N.Y.

[21] Appl. No.: 564,011

[22] Filed: Aug. 7, 1990

Related U.S. Application Data

[63] Continuation-in-part of Ser. No. 486,637, Feb. 28, 1990, Pat. No. 4,963,561.

[51] Int. Cl.$^5$ .................. C07D 471/04; A61K 31/44
[52] U.S. Cl. ........................................ 514/303; 546/118
[58] Field of Search ..................... 546/118; 514/303

[56] References Cited

U.S. PATENT DOCUMENTS

| | | | |
|---|---|---|---|
| 4,276,293 | 6/1981 | Lesher et al. | 546/118 |
| 4,294,837 | 10/1981 | Lesher et al. | 514/333 |
| 4,374,141 | 2/1983 | Lesher et al. | 514/334 |
| 4,963,561 | 10/1990 | Lesher et al. | 514/303 |

Primary Examiner—Robert W. Ramsuer
Assistant Examiner—Lenora Miltenberger
Attorney, Agent, or Firm—Philip E. Hansen; Paul E. Dupont

[57] ABSTRACT 1,3-dihydro-2H-imidazo[4,5-b]pyridin-2-ones having an aryl or heteroaryl group in the 6-position, useful as phosphodiesterase inhibitors, are prepared by reacting a 2-amino-5-(aryl or heteroaryl)pyridine-3-carboxylic acid with diphenylphosphoryl azide. The compounds are of the formula

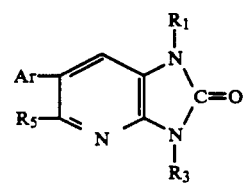

where $R_1$ and $R_3$ are hydrogen or lower-alkyl, $R_5$ is lower-alkyl or fluorinated lower-alkyl, and Ar is 4-or 3-pyridinyl, or N-oxides thereof, or phenyl or substituted phenyl.

5 Claims, No Drawings

IMIDAZOPYRIDINES, COMPOSITIONS AND USE

CROSS REFERENCE TO RELATED APPLICATIONS

This application is a continuation-in-part of our application Ser. No. 07/486,637 filed on Feb. 28, 1990 now U.S. Pat. No. 4,963,561.

BACKGROUND OF THE INVENTION (a) Field of the Invention:

The invention relates to novel 1,3-dihydro-2H-imidazo[4,5-b]pyridin-2-ones having an aryl or heteroaryl group in the 6-position, and to the preparation thereof and the use thereof as phosphodiesterase inhibitors.

(b) Information Disclosure Statement:

Lesher et al. U.S. Pat. No. 4,294,837, issued Oct. 13, 1981, discloses compounds of the formula:

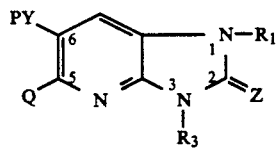

where Z is O or S, Q is hydrogen or lower-alkyl, $R_1$ and $R_3$ each are hydrogen, lower-alkyl, lower-hydroxyalkyl, 2,3-dihydroxypropyl, lower-alkoxyalkyl or Y-NB where Y is lower-alkylene having at least two carbon atoms between its connecting linkages and NB is di-(lower-alkyl)amino or 4-morpholinyl, at least one of $R_1$ or $R_3$ being hydrogen, and PY is 4- or 3-pyridinyl or 4- or 3-pyridinyl having one or two lower-alkyl substituents, or pharmaceutically-acceptable acid-addition salts thereof. The compounds of the above formula are useful as cardiotonic agents. At column 20, lines 26–27 is disclosed the compound 1,3-dihydro-5-methyl-6-(4-pyridinyl)-2H-imidazo[4,5-b]-pyridin-2-one, identified by name only.

SUMMARY OF THE INVENTION

In a composition of matter aspect the invention relates to compounds of the formula

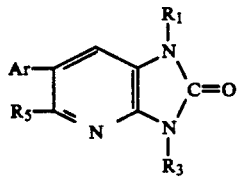

wherein $R_1$ and $R_3$ are hydrogen or lower-alkyl;

$R_5$ is lower-alkyl or fluorinated-lower-alkyl; and Ar is 4-or 3-pyridinyl, or N-oxides of 4-or 3-pyridinyl, 4-or 6-quinolinyl, 4-pyrimidinyl, phenyl, or phenyl substituted in the 4-position by OH, $NO_2$, $NH_2$, NH(lower-alkyl), N(lower-alkyl)$_2$, $NHSO_2$-(alkyl of 1-8 carbons), NH-$SO_2$-(phenyl or lower-alkylphenyl), NH-$SO_2$(fluorinated lower-alkyl), NH-$SO_2(CH_2)_4$N(lower-alkyl)$_2$, NH-$SO_2$-(8-quinolinyl), NHCO-lower-alkyl, NHCO(fluorinated lower-alkyl) or NHCONH-lower-alkyl; or in the 4-and 3-positions by OH and $NO_2$ or OH and $NH_2$, respectively;

and to pharmaceutically acceptable acid-addition salts thereof; with the proviso that when $R_5$ is unsubstituted lower-alkyl, Ar is other than 4-or 3-pyridinyl.

In a further composition of matter aspect, the invention relates to compositions for effecting phosphodiesterase inhibition in a mammalian organism comprising an effective amount of a compound of Formula I in admixture with suitable carriers or diluents.

In a still further composition of matter aspect the invention relates to intermediates in the preparation of compounds of Formula I.

In a process aspect, the invention relates to a process for preparing a compound of Formula I where $R_1$ and $R_3$ are hydrogen and Ar is 4-pyridinyl, 4-quinolinyl, 4-pyrimidinyl, phenyl or 4-nitrophenyl, which comprises reacting a compound of the formula

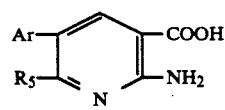

with a diphenylphosphoryl azide.

In a further process aspect, the invention relates to a method for effecting phosphodiesterase inhibition in a mammalian organism which comprises administering to said organism an effective amount of a compound of Formula I.

DETAILED DESCRIPTION INCLUSIVE OF PREFERRED EMBODIMENTS

The compounds of formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base (I) are not vitiated by side effects ascribable to the anions. In practicing the invention, it is convenient to use the free base form or the hydrochloride salt; however, appropriate pharmaceutically-acceptable salts within the scope of the invention are those derived from other mineral acids such as hydrobromic acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrobromide, sulfate, phosphate, sulfamate, acetate, citrate, lactate, tartrate, methanesulfonate, ethanesulfonate, benzenesulfonate, cyclohexylsulfamate and quinate, respectively.

The compounds of Formula I where at least one of $R_1$ and $R_3$ is hydrogen may exist in tautomeric equilibrium with the corresponding enol form:

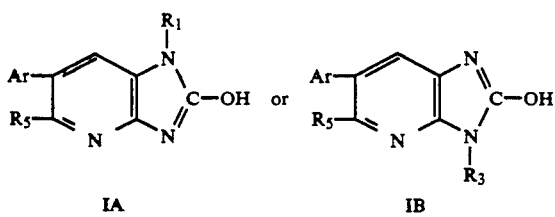

IA IB

While the compounds are believed to be predominantly in the keto form and will be represented as such throughout this specification, it is to be understood that the invention contemplates both forms and mixtures thereof.

The term "lower-alkyl" used in defining various substituents in Formula I is intended to include alkyl groups having from one to about six carbon atoms, which group can be straight or branched.

The term "fluorinated lower-alkyl" includes lower-alkyl groups containing one or more fluorine atoms. Representative of such groups are fluoromethyl, difluoromethyl, trifluoromethyl and pentafluoroethyl.

The reaction of a compound of Formula II with diphenylphosphoryl azide is preferably carried out in the presence of an organic base in an inert solvent at a temperature between about 50° and 150° C. The organic base is preferably a tertiary amine such as triethylamine. A preferred inert solvent is p-dioxane.

The intermediates of Formula II where $R_5$ is fluorinated alkyl are prepared by reacting ArCH=CH—N(alkyl)$_2$ with a fluorinated alkanoic acid anhydride $(R_5CO)_2O$ to obtain ArC(COR$_5$)=CH—N(alkyl)$_2$, heating the latter with AlkylOCOCH$_2$C(=NH)—OAlkyl to obtain alkyl 2-amino-5-Ar-6-R$_5$-3-pyridinecarboxylate, and hydrolyzing the latter to the free acid. Alkyl preferably has 1-6 carbon atoms.

The compounds of Formula II where $R_5$ is lower-alkyl and Ar is phenyl are prepared by conventional synthetic methods as illustrated by the Examples.

The compounds of Formula I where Ar is substituted phenyl can be prepared from compounds of Formula I where Ar is unsubstituted phenyl as follows:

Ar=4-nitrophenyl: by nitration of Ar=phenyl with nitric acid;

Ar=4-aminophenyl: by reduction of Ar=4-nitrophenyl, e.g. with stannous chloride, or by catalytic hydrogenation;

Ar=4-hydroxyphenyl: by diazotization and hydrolysis of Ar=4-aminophenyl;

Ar=4-(lower-alkylamino)phenyl or 4-(di-lower-alkylamino)phenyl: by alkylation of Ar=4-aminophenyl;

Ar=4-methylaminophenyl: by reaction of Ar=4-aminophenyl with formic acid followed by reduction of the intermediate where Ar=4-formylaminophenyl;

Ar=4-dimethylaminophenyl: by reaction of Ar=4-aminophenyl with formaldehyde under reducing conditions;

Ar=4-R'SO$_2$NHphenyl, where R' is alkyl of 1-8 carbons, phenyl or lower-alkylated phenyl, fluorinated lower-alkyl, (CH$_2$)$_4$N(lower-alkyl)$_2$ or 8-quinolinyl: by reaction of Ar=4-aminophenyl with R'SO$_2$Cl;

Ar=4-R"CONHphenyl, where R" is lower-alkyl or C(fluorinated lower-alkyl): by reaction of Ar=4-aminophenyl with R"COCl;

Ar=lower-alkyl-NHCONHphenyl: by reaction of Ar=4-aminophenyl with lower-alkyl—N=C=O;

Ar=4-hydroxy-3-nitrophenyl: by nitration of Ar=4-hydroxyphenyl;

Ar=3-amino-4-hydroxyphenyl: by reduction of Ar=4-hydroxy-3-nitrophenyl.

The compounds of formula I wherein Ar is a pyridine-N-oxide can be prepared from compounds of formula I wherein Ar is the corresponding pyridine by oxidation, preferably with m-chloroperbenzoic acid, in an inert solvent, preferably chloroform containing sufficient methanol to dissolve the starting material.

The following examples will further illustrate the invention.

Example 1

(a) 4-(2-Dimethylamino-1-ethenyl)pyridine [(CH$_3$)$_2$NCH=CH—C$_5$H$_4$N]

A solution of 47 g 4-picoline and 105.5 g bis(dimethylamino)methyl tertiary-butyl ether in 125 ml dimethylformamide (DMF) was heated at 140° C. under nitrogen for 18 hours. The solvent was removed in vacuo and the crystalline residue dissolved in boiling cyclohexane (about 3 L). The solution was filtered through filter paper containing charcoal and concentrated in vacuo to give 60 g (80%) 4-(2-dimethylamino-1-ethenyl)pyridine as light orange crystals.

(b) 4-(2-Dimethylamino-1-trifluoroacetyl-1-ethenyl)pyridine [(CH$_3$)$_2$NCH=C(COCF$_3$)C$_5$H$_4$N]

To a solution of 36 g 4-(2-dimethylamino-1-ethenyl)pyridine and 49 g triethylamine in 360 ml methylene dichloride held at 0° C. was added dropwise over a 1 hour period a solution of 56 g trifluoroacetic anhydride in 18 ml methylene dichloride. The reaction mixture was allowed to warm to 20° C. and stirred for 16 hours. The solvent was removed and the oily residue extracted with ether (5×600 ml). Silica gel (24 g) and magnesium sulfate (20 g) were added to the ether solution which was stirred and filtered. The filtrate was concentrated in vacuo and the residue solidified at 0° C. to give a yellow-orange oily solid. The latter was combined with the product of another run starting with 60 g of 4-(2-dimethylamino-1-ethenyl)pyridine and used directly in the next reaction (total crude product 180 g).

A sample of this product, when purified by column chromatography on silica, had the m.p. 82°-84° C.

(c) Ethyl 2-amino-5-(4-pyridinyl)-6-trifluoromethyl-3-pyridinecarboxylate

Diethyl iminomalonate [C$_2$H$_5$OCOCH$_2$C(=NH)OC$_2$H$_5$] hydrochloride (180 g, prepared as described in J. Am. Chem. Soc. 67, 1017 (1945)) was added slowly to an ice-cold mixture of 153 g sodium bicarbonate, 900 ml water and 540 ml ether with rapid stirring. The ether layer was separated and the aqueous layer extracted with ether. The combined ether solution was dried (Na$_2$SO$_4$) and concentrated to give 143.3 g diethyl iminomalonate as a colorless oil. The latter was mixed with the product of part (b) and stirred at 50° C. for 18 hours. The reaction mixture was dissolved in water (2 L), acidified with acetic acid and extracted with ether (3×1 L), dried (Na$_2$SO$_4$) and concentrated. The residue was dissolved in methylene dichloride and chromatographed on silica (ethyl acetate/hexane 1:5 and 1:3), followed by recrystallization from methylene dichloride/hexane to give 13.67 g of product as a colorless solid used directly in the following hydrolysis reaction. A purified sample of the product had the m.p. 121°–125° C.

(d) 2-Amino-5-(4-pyridinyl)-6-trifluoromethyl-3-pyridinecarboxylic acid [II; Ar=4-pyridinyl, R$_5$=CF$_3$]

A mixture of the product of part (c), 10% aqueous sodium hydroxide (75 ml) and 125 ml methanol was stirred at 100° C. for 6 hours. The reaction mixture was concentrated in vacuo and the residue neutralized with dilute acetic acid to pH 4–5. The solid product was collected, washed with water and dried to give 12.08 g of 2-amino-5-(4-pyridinyl)-6-trifluormethyl-3-pyridinecarboxylic acid as a colorless solid, m.p. above 283° C.(decompn.).

(e) 1,3-Dihydro-6-(4-pyridinyl)-5-trifluoromethyl-2H-imidazo[4,5-b]pyridin-2-one [I; Ar=4-pyridinyl, R$_1$ and R$_3$=H, R$_5$=CF$_3$]

A mixture of 12.08 g of the product of part (d), 15.26 g diphenylphosphoryl azide and 12 ml triethylamine in 240 ml p-dioxane was stirred at reflux for 6 hours. The reaction mixture was concentrated in vacuo and the residue treated with water (100 ml) and acetic acid (8 ml). The crude product was collected, washed with water and air dried to give 11.02 g of yellowish white solid. The latter was recrystallized from hot methanol to give 6.5 g of colorless solid. Further recrystallization from methanol and from acetone gave 4.2 g of pure 1,3-dihydro-6-(4-pyridinyl)-5-trifluoromethyl-2H-imidazo[4,5-b]pyridin-2-one, m.p. above 300° C.

(f) 1,3-Dihydro-6-(4-pyridinyl)-5-trifluoromethyl-2H-imidazo[4,5-b]pyridin-2-one N-(py)-oxide [I: Ar=

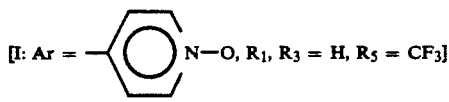

[I: Ar = ⟨pyridine ring⟩ N—O, R$_1$, R$_3$ = H, R$_5$ = CF$_3$]

Four grams of the product of part (e) was dissolved by gentle warming in 500 mL of chloroform and 50 mL of methanol. The solution was cooled and 3.58 g of m-chloroperbenzoic acid was added. The reaction was stirred at room temperature for 18 hours and the product, which had crystallized out, was filtered off and washed with chloroform to yield 3.5 g of 1,3-dihydro-6-(4-pyridinyl)-5-trifluoromethyl-2H-imidazo[4,5-b]pyridin-2-one N-(py)-oxide, mp>300°.

It is contemplated that the compound of part (e) can be alkylated with methyl iodide in the presence of sodium hydride to give 1,3-dihydro-1,3-dimethyl-6-(4-pyridinyl)-5-trifluoromethyl-2H-imidazo[4,5-b]pyridin-2-one [I; Ar=4-pyridinyl, R$_1$ and R$_3$=CH$_3$, R$_5$=CF$_3$].

EXAMPLE 2

Following the procedures of Example 1, but substituting pentafluoropropionic anhydride for the trifluoroacetic anhydride of Example 1, part (b), there were obtained the following:

(a) 4-(2-Dimethylamino-1-pentafluoropropionyl-1-ethenyl)pyridine [(CH$_3$)$_2$NCH=C(COC$_2$F$_5$)C$_5$H$_4$N], 92% yield, light yellow crystals, m.p. 105°–106° C. when recrystallized from methylene dichloride/hexane.

(b) Ethyl 2-amino-5-(4-pyridinyl)-6-pentafluoroethyl-3-pyridinecarboxylate, 24% yield, m.p. 125°–127° C.

(c) 2-Amino-5-(4-pyridinyl)-6-pentafluoroethyl-3-pyridinecarboxylic acid [II; Ar=4-pyridinyl, R$_5$=C$_2$F$_5$], 81% yield, yellow powder.

(d) 1,3-Dihydro-6-(4-pyridinyl)-5-pentafluoroethyl-2H-imidazo[4,5-b]pyridin-2-one [I; Ar=4-pyridinyl, R$_1$ and R$_3$=H, R$_5$=C$_2$F$_5$], yield 52%, m.p. above 290° C.(decompn.) when recrystallized from acetone/DMF.

EXAMPLE 3

Following the procedures of Example 1, but substituting 4-methylquinoline for the 4-picoline of Example 1, part (a), there were obtained the following:

(a) 4-(2-Dimethylamino-1-ethenyl)quinoline [known compound: Brederick et al. Chem. Ber. 101, 4048 (1968)].

(b) 4-(2-Dimethylamino-1-trifluoroacetyl-1-ethenyl)-quinoline, light yellow solid, recrystallized from methylene dichloride/hexane, m.p. 135°–137° C.

(c) Ethyl 2-amino-5-(4-quinolinyl)-6-trifluoromethyl-3-pyridinecarboxylate, 15% yield from compound of part (a), m.p. 204°–206° C. when recrystallized from methylene dichloride/hexane.

(d) 2-Amino-5-(4-quinolinyl)-6-trifluoromethyl-3-pyridinecarboxylic acid [II; Ar=4-quinolinyl, R$_5$=CF$_3$], pale yellow solid, obtained in 91% yield.

(e) 1,3-Dihydro-6-(4-quinolinyl)-5-trifluoromethyl-2H-imidazo[4,5-b]pyridine-2-one [I; Ar=4-quinolinyl, R$_1$ and R$_3$=H, R$_5$=CF$_3$], m.p.>300° C.(decompn.).

It is contemplated that following the procedures of Example 1 starting with 4-methylpyrimidine in place of 4-picoline there can be prepared 1,3-dihydro-6-(4-pyrimidinyl)-5-trifluoromethyl-2H-imidazo[4,5-b]pyridin-2-one [I; Ar=4-pyrimidinyl, R$_1$ and R$_3$=H, R$_5$=CF$_3$].

It is further contemplated that following the procedures of Example 1 starting with N-(2-phenyl-1-ethenyl)dimethylamine [C$_6$H$_5$CH=CHN(CH$_3$)$_2$] there can be prepared 1,3-dihydro-6-phenyl-5-trifluoromethyl-2H-imidazo[4,5-b]pyridin-2-one [I; Ar=C$_6$H$_5$, R$_1$ and R$_3$=H, R$_5$=CF$_3$].

EXAMPLE 4

(a) 2-Chloro-3-cyano-6-methyl-5-phenylpyridine

A mixture of 100.34 g 3-cyano-6-methyl-5-phenyl-1H-pyridin-2-one [Walker and Weaver, J. Org. Chem. 26, 4441 (1961)] and 192 ml phenylphosphonic dichloride (C$_6$H$_5$POCl$_2$) was warmed to 160°–170° C. and kept at that temperature for about 16 hours. The reaction mixture was cooled and poured into ice water. The solid product was collected, dried in a vacuum oven and extracted with ether. The ether solution was concentrated, and the residue was washed with hexane and extracted with 300 ml 15% aqueous potassium bicarbonate. The resulting solid was dried in a vacuum oven to give 92.71 g (85%) 2-chloro-3-cyano-6-methyl-5-phenylpyridine, m.p. 134°–135° C.

(b) 2-Amino-6-methyl-5-phenyl-3-pyridinecarboxylic acid [II; Ar=C$_6$H$_5$, R$_3$=H, R$_5$=CH$_3$]

A mixture of 92.71 g 2-chloro-3-cyano-6-methyl-5-phenylpyridine, 1000 ml concentrated ammonium hydroxide and 400 ml ethanol was heated in an autoclave at 185° C. for 30 hours. The reaction mixture was cooled in ice, neutralized with acetic acid and stirred at room temperature for 2 hours. The solid product was collected, washed with water (800 ml) and a small amount of ethanol, and dried in a vacuum oven at 85° C. to give 75.61 g (82%) of 2-amino-6-methyl-5-phenyl-3-pyridinecarboxylic acid, m.p. 298°–300° C.

(c) 1,3-Dihydro-5-methyl-6-phenyl-2H-imidazo[4,5-b]pyridin-2-one [I; Ar=C$_6$H$_5$, R$_1$ and R$_3$=H, R$_5$=CH$_3$].

A mixture of 9.92 g 2-amino-6-methyl-5-phenyl-3-pyridinecarboxylic acid, 13.13 ml diphenylphosphoryl azide, 11.6 ml triethylamine and 200 ml p-dioxane was heated at reflux for about 16 hours. The reaction mixture was cooled, and the solid which precipitated was collected and dried (air-drying and vacuum oven) to give 4.81 g of product. The filtrate was concentrated and the residue treated with 450 ml 15% potassium bicarbonate solution to give, after filtration and drying, an additional 4.21 g of product: total yield 9.02 g (93%) of 1,3-dihydro-5-methyl-6-phenyl-2H-imidazo[4,5-b]pyridin-2-one, m.p. above 300° C.

EXAMPLE 5

1,3-Dihydro-5-methyl-6-(4-nitrophenyl)-2H-imidazo[4,5-b]pyridin-2-one [I; Ar=4-O$_2$NC$_6$H$_4$, R$_1$ and R$_3$=H, R$_5$=CH$_3$]

1,3-Dihydro-5-methyl-6-phenyl-2H-imidazo[4,5-b]pyridin-2-one (Example 4c, 8.06 g) was added in small portions to 80 ml 90% nitric acid cooled to −2° C. The reaction mixture was stirred at 0° C. for 2 hours and then poured portionwise into ice-water. The solid product was collected, washed with water and ether, and dried in high vacuum at 110°–130° C. to give 9.3 g (97%) of 1,3-dihydro-5-methyl-6-(4-nitrophenyl)-2H-imidazo[4,5-b]pyridin-2-one, m.p. above 300° C. Further purification was accomplished by repeated recrystallization from aqueous dimethylformamide.

EXAMPLE 6

6-(4-Aminophenyl)-1,3-dihydro-5-methyl-2H-imidazo[4,5-b]pyridin-2-one [I; Ar=4-H$_2$NC$_6$H$_4$, R$_1$ and R$_3$=H, R$_5$=CH$_3$]

To a suspension of 10.11 g 1,3-dihydro-5-methyl-6-(4-nitrophenyl)-2H-imidazo[4,5-b]pyridin-2-one (Example 5) in 200 ml absolute ethanol and 80 ml water was added 25.34 g stannous chloride dihydrate (SnCl$_2$.2H$_2$O) and 120 ml concentrated hydrochloric acid. The reaction mixture was heated at reflux for 6 hours, then cooled to room temperature and allowed to stand until crystals formed. The latter was collected by decantation and additional product obtained by concentration of the mother liquors to 60% of the original volume. The total solid product was washed with ethanol and ether and dried (high vacuum at 120° C.) to give 11.52 g 6-(4-aminophenyl)-1,3-dihydro-5-methyl-2H-imidazo[4,5-b]pyridin-2-one in the form of its hydrochloride salt and containing ethanol of crystallization, m.p. 277°–283° C.

Alternative preparation: To a solution of 21.40 g 1,3dihydro-5-methyl-6-(4-nitrophenyl)-2H-imidazo[4,5-b]pyridin-2-one in 1000 ml DMF was added 2.05 g palladium-on-carbon catalyst, and the mixture was hydrogenated in a Parr reactor at 50 psi and room temperature. After 90 min. the reaction was complete and the mixture was filtered and concentrated in vacuo. The residue was washed with water and dried in a vacuum oven to give an essentially quantitative yield of 6-(4-aminophenyl)-1,3-dihydro-5-methyl-2H-imidazo[4,5-b]pyridin-2-one in the free base form, m.p. above 300° C.

It is contemplated that 6-(4-aminophenyl)-1,3-dihydro-5-methyl-2H-imidazo[4,5-b]pyridin-2-one can be alkylated by reacting it with formic acid followed by reduction of the intermediate formylamino derivative to obtain 6-[4-(methylamino)phenyl]-1,3-dihydro-5-methyl-2H-imidazo[4,5-b]pyridin-2-one [I; Ar=4-CH$_3$NHC$_6$H$_4$, R$_1$ and R$_3$=H, R$_5$=CH$_3$]; or by reacting it with formaldehyde under reducing conditions to obtain 6-[4-(dimethylamino)phenyl]-1,3-dihydro-5-methyl-2H-imidazo[4,5-b]pyridin-2-one [I; Ar=4-(CH$_3$)$_2$NC$_6$H$_4$, R$_1$ and R$_3$=H, R$_5$=CH$_3$].

EXAMPLE 7

1,3-Dihydro-5-methyl-6-[4-(trifluoroacetylamino)phenyl]-2H-imidazo[4,5-b]pyridin-2-one [I; Ar=4-F$_3$CCONHC$_6$H$_4$, R$_1$ and R$_3$=H, R$_5$=CH$_3$]

To a suspension of 3.03 g 6-(4-aminophenyl)-1,3-dihydro-5-methyl-2H-imidazo[4,5-b]pyridin-2-one hydrochloride and 2 ml triethylamine in 50 ml pyridine cooled in an ice bath was added dropwise 1.86 ml trifluoroacetic anhydride. The reaction mixture was stirred 40 min at 0° C. and then at room temperature for about 20 hours. The reaction mixture was concentrated in vacuo, and the residue was treated with water, filtered, washed with ethanol and ether and dried at 90° C. for 2 hours in high vacuum. The product was recrystallized from acetonitrile-DMF to give 1.18 g 1,3-dihydro-5-methyl-6-[4-(trifluoroacetylamino)phenyl]-2H-imidazo[4,5-b]pyridin-2-one, m.p. above 300° C.

EXAMPLE 8

6-[4-(Acetylamino)phenyl]-1,3-dihydro-5-methyl-2H-imidazo[4,5-b]pyridin-2-one [I; Ar=4-CH$_3$CONHC$_6$H$_4$, R$_1$ and R$_3$=H, R$_5$=CH$_3$] was prepared from 1.73 g 6-(4-aminophenyl)-1,3-dihydro-5-methyl-2H-imidazo[4,5-b]pyridin-2-one hydrochloride and 0.65 ml acetic anhydride according to the procedure of Example 7, and was obtained in 90% yield as a colorless solid, m.p. above 300° C. when recrystallized from aqueous DMF.

EXAMPLE 9

1,3-Dihydro-6-[4-(methanesulfonylamino)phenyl]-5-methyl-2H-imidazo[4,5-b]pyridin-2-one [I; Ar=4-CH$_3$SO$_2$NHC$_6$H$_4$, R$_1$ and R$_3$=H, R$_5$=CH$_3$] was prepared from 1.51 g 6-(4-aminophenyl)-1,3-dihydro-5-methyl-2H-imidazo[4,5-b]pyridin-2-one hydrochloride and 0.63 ml methanesulfonyl chloride according to the procedure of Example 7, and was obtained in 69% yield as a colorless solid, m.p. above 300° C. when recrystallized from aqueous DMF and digested with methanol.

EXAMPLE 10

6-[4-(Butanesulfonylamino)phenyl]-1,3-dihydro-5-methyl-2H-imidazo[4,5-b]pyridin-2-one [I; Ar=4-CH$_3$(CH$_2$)$_3$SO$_2$NH-C$_6$H$_4$, R$_1$ and R$_3$=H, R$_5$=CH$_3$] was prepared from 1.5 g 6-(4-aminophenyl)-1,3-dihydro-5-methyl-2H-imidazo[4,5-b]pyridin-2-one hydrochloride and 0.91 ml butanesulfonyl chloride according to the procedure of Example 7, and was obtained (0.92 g) as a colorless solid, m.p. above 300° C. when recrystallized from ethanol.

EXAMPLE 11

6-[4-(Butanecarbonylamino)phenyl]-1,3-dihydro-5-methyl-2H-imidazo[4,5-b]pyridin-2-one [I; Ar=4-$CH_3(CH_2)_3CONH-C_6H_4$, $R_1$ and $R_3$=H, $R_5$=$CH_3$] was prepared from 3 g 6-(4-aminophenyl)-1,3-dihydro-5-methyl-2H-imidazo[4,5-b]pyridin-2-one hydrochloride and 1.86 ml valeryl chloride according to the procedure of Example 7, and was obtained (1.16 g) as a colorless solid, m.p. above 300° C. when recrystallized from ethanol.

EXAMPLE 12

1,3-Dihydro-5-methyl-6-[4-(p-toluenesulfonylamino)phenyl]-2H-imidazo[4,5-b]pyridin-2-one [I; Ar=4-(4-$CH_3C_6H_4$-$SO_2NH)C_6H_4$, $R_1$ and $R_3$=H, $R_5$=$CH_3$] was prepared from 3.88 g 6-(4-aminophenyl)-1,3-dihydro-5-methyl-2H-imidazo[4,5-b]pyridin-2-one hydorchloride and 5.5 g p-toluenesulfonyl chloride according to the procedure of Example 7, and was obtained (1.05 g) as a colorless solid, m.p. above 300° C. after repeated recrystallization from ethanol.

EXAMPLE 13

1,3-Dihydro-6-[4-(hexanesulfonylamino)phenyl]-5-methyl-2H-imidazo[4,5-b]pyridin-2-one [I; Ar=4-$CH_3(CH_2)_5SO_2NH-C_6H_4$, $R_1$ and $R_3$=H, $R_5$=$CH_3$] was prepared from 3 g 6-(4-aminophenyl)-1,3-dihydro-5-methyl-2H-imidazo[4,5-b]pyridin-2-one hydrochloride and 3.42 g n-hexanesulfonyl chloride according to the procedure of Example 7, and was obtained (0.91 g) as an amorphous solid from methanol/ethyl acetate.

EXAMPLE 14

1,3-Dihydro-6-[4-(8-quinolinylsulfonylamino)phenyl]-5-methyl-2H-imidazo[4,5-b]pyridin-2-one [I; Ar=4-(8-quinolinyl$SO_2NH)C_6H_4$, $R_1$ and $R_3$=H, $R_5$=$CH_3$] was prepared from 2.92 g 4-(4-aminophenyl)-1,3-dihydro-5-methyl-2H-imidazo[4,5-b]pyridin-2-one hydrochloride and 8-quinolinylsulfonyl chloride according to the procedure of Example 7, and was obtained in 64% yield, m.p. above 300° C. when recrystallized from aqueous DMF and digested in methanol.

EXAMPLE 15

1,3-Dihydro-6-[4-(N'-propylureido)phenyl]-5-methyl-2H-imidazo[4,5-b]pyridin-2-one [I; Ar=4-$CH_3(CH_2)_2NHCONHC_6H_4$, $R_1$ and $R_3$=H, $R_5$=$CH_3$]

A mixture of 2.52 g 4-(4-aminophenyl)-1,3-dihydro-5-methyl-2H-imidazo[4,5-b]pyridin-2-one hydrochloride, 1.28 ml n-propyl isocyanate and 25 ml N-methyl-2-pyrrolidone was heated on a steam bath for two hours. The reaction mixture was poured into ice-water, collected by filtration and washed with water and ether. The solid product was recrystallized from aqueous DMF and dried in vacuo to give 0.59 g 1,3-dihydro-6-[4-(N'-propylureido)phenyl]-5-methyl-2H-imidazo[4,5-b]pyridin-2-one, m.p. above 300° C.

EXAMPLE 16

1,3-Dihydro-6-(4-hydroxyphenyl)-5-methyl -2H-imidazo[4,5-b]pyridin-2-one [I; Ar=4-$HOC_6H_4$, $R_1$ and $R_3$=H, $R_5$=$CH_3$]

To a solution of 4.77 g 4-(4-aminophenyl) -1,3-dihydro-5-methyl-2H-imidazo[4,5-b]pyridin -2-one hydrochloride in 75 ml 1:1 $H_2O/H_2SO_4$ cooled to 5° C. was added dropwise a solution of 1.19 sodium nitrite in 9 ml water over a period of 15 min. The reaction mixture was warmed to 70° C. for 10 min. until evolution of gas ceased and then made basic with sodium hydoxide solution. The product was obtained in a series of fractions (total yield 1.75 g). A sample when recrystallized from aqueous methanol had a m.p. above 300° C.

It is further contemplated that 4-(4-aminophenyl)-1,3-dihydro-5-methyl-2H-imidazo[4,5-b]pyridin-2-one hydrochloride can similarly be caused to react with trifluoromethylsulfonyl chloride or 4-dimethylaminobutylsulfonyl chloride to obtain, respectively, 1,3-dihydro-6-(4-trifluoromethylsulfonylaminophenyl)-5-methyl-2H-imidazo[4,5-b]pyridin-2-one [I; Ar=4-$CF_3SO_2NHC_6H_4$, $R_1$ and $R_3$=H, $R_5$=$CH_3$], and 1,3-dihydro-6-[4-(4-dimethylamino-butyl)sulfonylaminophenyl]-5-methyl-2H-imidazo[4,5-b]pyridin-2-one [I; Ar=$(CH_3)_2N(CH_2)_4SO_2NHC_6H_4$, $R_1$ and $R_3$=H, $R_5$=$CH_3$].

It is further contemplated that 1,3-dihydro-6-b 6-(4-hydroxyphenyl)-5-methyl-2H-imidazo [4,5-b] pyridin-2-one (Example 16) can be nitrated with nitric acid to obtain 6-(4-hydroxy-3-nitrophenyl)-1,3-dihydro-5-methyl-2H-imidazo[4,5-b]pyridin-2-one [I; Ar=3-$O_2N$-4-$HOC_6H_3$, $R_1$ and $R_3$=H, $R_5$=$CH_3$], which in turn can be reduced by catalytic hydrogenation to obtain 6-(3-amino-4-hydroxyphenyl)-1,3-dihydro-5-methyl-2H-imidazo[4,5-b]pyridin-2-one [I; Ar=3-$H_2N$-4-$HOC_6H_3$, $R_1$ and $R_3$=H, $R_5$=$CH_3$].

Multiple isozymic forms of cyclic nucleotide phosphodiesterase (PDE) exist in most tissues. Recently developed cardiotonic agents have been shown to selectively inhibit the "low Km" cAMP form of PDE (also referred to as peak III PDE) from cardiac muscle. A "low Km" cGMP form of PDE (also referred to as peak I PDE) also has been identified. Increases in cAMP and cGMP will relax both vascular smooth and bronchial smooth muscle. Selective PDE isozyme inhibition represents a novel subcellular mechanism by which increses in cAMP or cGMP and subsequent vaso- or broncho-relaxation may be achieved. Moreover, a component of positive inotropy may be retained, dependent upon the isozyme or tissue source specificity of an inhibitor. Thus, development of PDE isozyme inhibitors represents novel approaches for the discovery of agents useful for treating hypertension, congestive heart failure or asthma. For example, compounds having essentially high PDE III inhibitory activity are expected to have cardiotonic and vasodilatory (antihypertensive) activity. PDE isozymes (peak I and III) are isolated from canine aortic smooth, ventricular or tracheal smooth muscle sources by DEAE - cellulose column chromatography. Inhibition of both peaks by a putative inhibitor from any of these sources is quantitated. If $\geq$50% inhibition is detected at 30 $\mu$M, then an $IC_{50}$ value and corresponding 95% confidence limits for both peaks is determined.

The procedures for the separation of the isozymes of PDE from animal tissue and the testing of the compounds of the invention for phosphodiesterase inhibition are essentially those described by Weishaar et al., *Biochem. Pharmacol.* 35:787-800 (1986) and Thompson et al., *Adv. Cyclic Nucleotide Res.* 10:69-92. Initial screening of test compounds with both peak I and peak III PDE isozymes is done at a concentration of 10, 30 or 100 μm, and each assay is performed in triplicate for each inhibitor. The IC$_{50}$ values (concentration causing 50% inhibition) are then calculated from concentration-response curves as described by Tallarida and Murray, *Manual of Pharmacologic Calculations with Computer Programs*, Procedure 8, Graded Dose-Response, pp. 14–19, Springer-Verlag, New York, 1981.

Test results for the compounds of the invention are given in the following Table.

| Example No. | Percent Inhibition at Given μM or IC$_{50}$ (μM) | |
|---|---|---|
| | PDE I | PDE III |
| 1(e) | 52.9 μM | 0.023 μM |
| 1(f) | 0%/1 μM | 0.029 μM |
| 2(d) | 12 μM | 1.8 μM |
| 3(e) | 4%/100 μM | 9%/1 μM |
| 4(c) | 38%/1000 μM | 0.27 μM |
| 5 | 35%/300 μM | 0.009 μM |
| 6 | 45 μM | 0.5 μM |
| 7 | 63.6 μM | 0.63 μM |
| 8 | 22%/30 μM | 0.62 μM |
| 9 | 45 μM | 0.47 μM |
| 10 | 9 μM | 0.094 μM |
| 11 | 0%/1 μM | 37%/1 μM |
| 12 | 13%/1 μM | 64%/1 μM |
| 13 | 5.6 μM | 0.053 μM |
| 14 | 1.6 μM | 0.055 μM |
| 15 | 319 μM | 0.104 μM |

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

We claim:

1. A compound of the formula

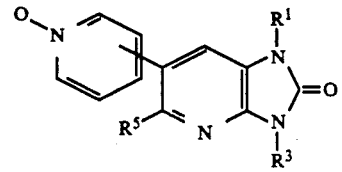

wherein

R$_1$ and R$_3$ are hydrogen or lower-alkyl;

R$_5$ is lower-alkyl or fluorinated lower-alkyl; and the pyridine-N-oxide is attached at the 4- or 3-position; or a pharmaceutically acceptable acid-addition salt thereof.

2. 1,3-Dihydro-6-(4-pyridinyl)-5-trifluoromethyl-2H-imidazo[4,5-b]pyridin-2-one N-(py)-oxide according to claim 1.

3. A composition for effecting phosphodiesterase inhibition in a mammalian organism which comprises an effective amount of a compound according to claim 1 in admixture with a suitable carrier or diluent.

4. A method of treating congestive heart failure or hypertension in a mammalian organism which comprises administering to said organism a composition according to claim 3.

5. A method for effecting phosphodiesterase inhibition in a mammalian organism which comprises administering to said organism a composition according to claim 3.

* * * * *